US010537270B2

(12) United States Patent
Sarussi et al.

(10) Patent No.: US 10,537,270 B2
(45) Date of Patent: Jan. 21, 2020

(54) METHOD AND DEVICE FOR OPTICAL MEASUREMENT OF BIOLOGICAL PROPERTIES

(71) Applicant: BIOBEAT TECHNOLOGIES LTD, Zoran (IL)

(72) Inventors: Israel Sarussi, Nahal Sorek (IL); Arik Ben-Yishai, Zoran (IL); Johanan May, Petach Tikva (IL)

(73) Assignee: BIOBEAT TECHNOLOGIES LTD, Zoran (IL)

( * ) Notice: Subject to any disclaimer, the term of this patent is extended or adjusted under 35 U.S.C. 154(b) by 443 days.

(21) Appl. No.: 15/218,123

(22) Filed: Jul. 25, 2016

(65) Prior Publication Data
US 2018/0020960 A1   Jan. 25, 2018

(51) Int. Cl.
*A61B 5/1455* (2006.01)
*A61B 5/026* (2006.01)
(Continued)

(52) U.S. Cl.
CPC ........ *A61B 5/14552* (2013.01); *A61B 5/0261* (2013.01); *A61B 5/4266* (2013.01);
(Continued)

(58) Field of Classification Search
CPC ... A61B 5/14552; A61B 5/021; A61B 5/0261; A61B 5/029; A61B 5/14532;
(Continued)

(56) References Cited

U.S. PATENT DOCUMENTS

| 2010/0130840 A1* | 5/2010 | Isaacson ............ A61B 5/14553 600/323 |
| 2012/0197093 A1* | 8/2012 | LeBoeuf ................ G16H 40/63 600/301 |

(Continued)

OTHER PUBLICATIONS

Nogawa et al., New Hybrid Reflectance Optical Pulse Oximetry Sensor for Lower Oxygen Saturation Measurement and for Broader Clinical Application, SPIE vol. 2976, Biomedical Sensing, Imaging and Tracking Technologies II, p. 78-87, dated Jun. 16, 1997.*

(Continued)

*Primary Examiner* — Eric F Winakur
*Assistant Examiner* — Marjan Fardanesh
(74) *Attorney, Agent, or Firm* — Soroker Agmon Nordman (57) ABSTRACT

The subject matter discloses a device for measuring biological properties of an examined tissue, the device comprising at least one light source configured and operable to illuminate the examined tissue with light radiation of one or more wavelengths at a certain light illumination direction; and a light detector located at a same side of said examined tissue and configured and operable to receive light components of said one or more wavelengths reflected from the examined tissue in response to the illuminated light radiation at a certain light detection direction, and to generate measurement data indicative thereof; at least one of said light illumination direction and detection direction is positioned at an angle of at least 2° relative to an imaginary line perpendicular to the examined tissue or form an angle of at least 2° between the light illumination direction and detection direction.

18 Claims, 6 Drawing Sheets

(51) Int. Cl.
*A61B 5/00* (2006.01)
*G01N 33/49* (2006.01)
*A61B 5/021* (2006.01)
*A61B 5/029* (2006.01)
*A61B 5/145* (2006.01)

(52) U.S. Cl.
CPC ........... *A61B 5/742* (2013.01); *G01N 33/492* (2013.01); *G01N 33/4925* (2013.01); *A61B 5/021* (2013.01); *A61B 5/029* (2013.01); *A61B 5/14532* (2013.01); *A61B 5/14546* (2013.01); *A61B 5/4872* (2013.01); *A61B 2562/0238* (2013.01)

(58) Field of Classification Search
CPC . A61B 5/14546; A61B 5/4266; A61B 5/4872; A61B 5/742; A61B 2562/0238; G01N 33/492; G01N 33/4925
See application file for complete search history.

(56) References Cited

U.S. PATENT DOCUMENTS

| | | | |
|---|---|---|---|
| 2014/0058272 A1* | 2/2014 | Naing | A61B 5/7207 600/479 |
| 2014/0275852 A1* | 9/2014 | Hong | A61B 5/02427 600/301 |
| 2015/0094552 A1* | 4/2015 | Golda | A61B 5/04325 600/336 |
| 2016/0061726 A1* | 3/2016 | Ness | G01N 21/55 600/476 |

OTHER PUBLICATIONS

Vishay Telefunken, "Physics and Technology of Emitters and Detectors", Dec. 1999, p. 11-24.*
Maattala et al., Optimum Place for Measuring Pulse Oximeter Signal in Wireless Sensor-Belt or Wrist Band, ICCIT.2007.63, IEEE, pp. 1856-1861, 2007 (Year: 2007).*

* cited by examiner

METHOD AND DEVICE FOR OPTICAL MEASUREMENT OF BIOLOGICAL PROPERTIES

TECHNOLOGICAL FIELD

The present invention is generally in the field of optical measurement of biological properties of an examined subject, and blood related parameters and properties in particular.

BACKGROUND

The majority of optical blood pulse measurements (e.g., pulse oximetry) are carried out nowadays utilizing transmissive measurement techniques requiring sensor devices that are mountable over two opposite sides of a thin body part/organ (e.g., finger tip or earlobe). Particularly, transmissive measurement techniques use a light source typically placed on one side of the body part/organ for irradiating light signals thereover, and a light detector placed on the other side of the body part/organ to measure the intensity of light signals passing through it.

However, there are various advantages for reflective blood measurement techniques, which are considered to be preferable in certain applications, particularly in types of wearable medical devices, such as medical watches, for example. Some of the advantages of reflective blood measurement techniques include, inter alia, the ability to conduct optical measurements on almost any part of the body, including thick organs. Other outstanding advantages are associated with the reduced energy consumption of reflective measurement techniques stemming from the minimal energy consumption required to reflect light from tissue layers, as opposed to transmissive techniques where the light is required to pass through the entire width of the organ.

There are however various limitations associated with the reflective measurement techniques, such as low signal-to-noise ratios (SNR), the low AC/DC ratios (Wherein AC is light waves reflected from (capillary) blood vessels, and DC is a combination of light waves reflected from other parts of the examine organ tissue and light waves reflected directly from the organ surface without passing through the examine tissue. Attempts to overcome these limitations of the reflective measurement techniques by increasing the power of the irradiated light (e.g., by increasing the electrical current supplied to the light source, and/or by increasing the number of light sources), typically also result in respective increase of noise components in the measured signals (due to respective increase of the baseline DC component), and thus do not provide satisfying results. There is thus a need to improve the quality of optical signals measured by reflective blood measurements techniques, to provide higher AC/DC ratios and improve the signal-to-noise ratios of the measured signals.

Some reflective measurements techniques known from the patent literature are briefly described herein below.

US Patent Publication No. 2009/082642 discloses a system and method for use in monitoring of biological parameters of a subject. The system includes an illumination unit including at least one light source of at least one pre-selected wavelength band, to be applied to a selected region in the subject; and a detection system configured for measuring reflections of the light at different angles and different spatial locations with respect to the illuminated region. The detection system is configured and operable to detect spatially separated light components corresponding to the specular dependent component of the signal and the pulsatile related diffused component of the signal coming from the subject in different directions respectively, thereby defining at least two independent channels of information, enabling identification of the reflected signal part dependent on motion effects.

US Patent Publication No. 2014/213917 describes a biofeedback device and a light sensor thereof that can be mounted on or integrated with eyewear such as swimming goggles. The biofeedback device may include a heart rate measurement apparatus comprising a reflected green light sensor, and first, second, and third green light emission elements. The biofeedback device may include a housing having a first portion and a second portion, which each of the first and second portions having a first side and a second side. At least a portion of the heart rate measurement apparatus may be disposed within the housing first portion and may be exposed through an opening in the second side of the housing first portion. The biofeedback device may also include an opening that allows the device to be removably engageable with at least a portion of the swimming goggles.

Chinese Paten publication No. 102198005 describes a reflective wrist oximeter with an electrocardiograph function, which comprises a blood oxygen acquisition module, an electrocardiosignal acquisition module, a processing module, a display module, a shell and wrist bands, wherein the blood oxygen acquisition module comprises a light-emitting driver, a light-emitting tube and a photosensor; the light-emitting tube and the photosensor are arranged at the same side of a position to be detected, and an included angle having preset degrees is formed between the light-emitting tube and the photosensor; the electrocardiosignal acquisition module comprises a first electrode and a second electrode and is used for acquiring electrocardiosignals; the processing module is used for processing pulse blood oxygen data acquired by the acquisition module and the electrocardiosignals acquired by the electrocardiosignal acquisition module; the display module is used for displaying information processed by the processing module to a user; the wrist bands are connected to both sides of the shell; the first electrode is arranged at one side of the shell, which is in contact with the wrist; the display module is arranged at the other side of the shell, which is opposite to the first electrode; the second electrode is arranged outside the display module; and the blood oxygen acquisition module is arranged inside or outside the second electrode. The reflective wrist oximeter delicately combines the reflective blood oxygen technology and the electrocardiograph technology, and is convenient to operate.

SUMMARY OF THE INVENTION

The present invention discloses a device designed for optical measurement of biological properties of a subject employing a reflective measurement techniques. The reflective measurement techniques disclosed herein can be useful for measuring blood properties (e.g., heart rate, blood parameters and/or blood analyses concentration/level) in a living tissue of the examined subject. The optical measurement device and techniques disclosed herein overcome the deficiencies associated with the conventional measurement setups by arranging one or more light sources of the reflective measurement device in certain orientations and distances relative to a light detector unit of the device's setup. Proper selection of the direction and distances of the one or more light sources relative to the light detector (or one more light detectors relative to the light source) substantially improves the magnitudes, the SNR and the AC/DC ratios, of the measured optical signals.

Optical signals measured by reflective measurement techniques can be substantially improved by properly setting a distance between a light source and a light detection unit of the device, and an angle between their light detector and light illumination directions. In this way most of the light components reaching the light detector are reflected/scattered from perfused layers of the illuminated tissue (also referred to herein as remote tissue layers), and that most of the light components reflected/scattered from non-perfused layers of the illuminated tissue (also referred to herein as near-surface tissue layers) don't reach the detector, and thus not measured.

Therefore, embodiments of the present invention provide that the majority of the light components detected by the light detection unit are scattered from tissue layers comprising blood vessels, and therefore contain more information about the blood flowing through the examined tissue (i.e., the pulsating AC component). On the other hand, since many of the light components reflected/scattered from non-perfused tissue layers do not reach the detector and therefore not measured, the DC component of the measured signals is substantially reduced, which provides for substantial increase of the SNR and the AC/DC ratios of the measured signals.

In possible measurement setups of the measurement device, according to some possible embodiments at least one light source is used to emit light of one or more predetermined wavelength ranges over an examined tissue. At least one adjacently located light detector is used to detect light radiation of said one or more predetermined wavelength ranges reflected from the illuminated tissue. The at least one light source and the at least one light detector are arranged in a spaced apart relationship to attain certain distances therebetween, and in predefined orientations one relative to the other to attain a certain angle between their respective illumination and detection directions.

In some embodiments of the device configuration disclosed herein, the certain distances and predefined orientations between the light source(s) and light detector(s) of the reflective measurement device are configured such that only light components within a predetermined range of angular reflections can reach the light detector and contribute to the measured optical signals. This device's configuration thereby reduces, or in some cases, substantially prevents, collection of light components directly reflected from the organ surface (e.g., stratum corneum) without passing through any layer of the examine tissue, and/or reflected scattered light components from non-perfused upper layers of the examined tissue, and the like. The above two components (directly surface reflection and non-perfused upper layers reflection) are the main DC components. Thereby a reduction at those components directly increase the AC/DC ratio. In some other exemplary embodiments of the present invention the reflective measurement device may be configured to increase the light emission. Such configuration can lengthen the optical path of the emitted light in a given tissue layer, thereby increase the light scattering, and enhance the probability to collect light components reflected from the perfused tissue layer.

In some possible embodiments the reflective measurement device may comprise a plurality of light sources (e.g., 2, 3 or 4, or more) arranged around a light detector, such that each of the light sources can direct emitted light away from the direction of the light collection of the light detector. It is however noted that in some embodiments the reflective measurement device can be configured with acceptable good results using a single light source. In addition, in possible embodiments of the present invention several light detectors may be used to collect the light components reflected from examined tissue as the direction and distance of the light sources relative to the light detectors of the device, may be within acceptable ranges of said certain distances and predefined directions of the measurement device.

Embodiments of the present invention may be used to implement wearable devices to be worn over a portion of body segments of a subject, such as, but not limited to, head neck, torso, or limbs (e.g., over the wrist, like a watch).

The biological properties measured by the measurement device of the present invention may comprise heart rate, blood flow, arterial blood oxygen saturation, and various blood related parameters such as concentration of a substance/analyte (e.g., sugar, cholesterol, hemoglobin, bilirubin) in blood, cardiac parameters, and the like. Thus, in some possible embodiment, the light source is configured to illuminate the examined tissue with multiple wavelengths selected for enabling determination of one or more biological properties of the subject.

1. It is an object of the present invention to disclose a device for measuring biological properties of an examined tissue, the device comprising, at least one light source configured and operable to illuminate the examined tissue with light radiation of one or more wavelengths at a certain light illumination direction; and a light detector located at a same side of said examined tissue and configured and operable to receive light components of said one or more wavelengths reflected from the examined tissue in response to the illuminated light radiation at a certain light detection direction, and to generate measurement data indicative thereof; at least one of said light illumination direction and detection direction is positioned at an angle of at least $2°$ relative to an imaginary line perpendicular to the examined tissue or form an angle of at least $2°$ between the light illumination direction and detection direction.

In some cases, the direction of light detector is substantially perpendicular to the surface of the examined tissue and the direction of light source is positioned at an angle of at least 2 degrees from the direction of light detector.

In some cases, the direction of light source is substantially perpendicular to the surface of the examined tissue and the direction of light detector is positioned at an angle of at least 2 degrees from the direction of light source.

In some cases, the at least one light source is oriented so as to direct the light illumination away from the light detector.

In some cases, the at least one light source is oriented so as to direct the light illumination towards the light detector.

In some cases, the at least one light source is parallel to the light detector and is positioned at an angle of at least $2°$ relative to an imaginary line perpendicular to the examined tissue.

In some cases, the at least one light source is not parallel to the light detector, wherein each of the light source and the light detector forms an angle of at least $2°$ relative to an imaginary line perpendicular to the examined tissue.

In some cases, the distance between the at least one light source and the light detector is 0.1 to 30 mm.

In some cases, the angle formed between the light illumination and detection directions is decreased in response to an increase in a distance between the at least one light source and the light detector.

In some cases, the device further comprises two or more light sources encircling the light detector.

In some cases, the biological properties include at least one of heart rate, oxygen saturation, hemoglobin level, blood pressure, cardiac output, stroke volume, perspiration, glucose/sugar level, and bilirubin level, fat level.

In some cases, the device is a wearable device comprising a housing having bottom and upper sides and strapping means for attaching said bottom side of the housing to an examined tissue of said subject.

In some cases, the housing comprises at said bottom side of said housing, at least one light source configured and operable to illuminate said examined tissue with light radiation of one or more wavelengths at a certain light illumination direction, and a light detector configured and operable to receive light components of said one or more wavelengths reflected from the examined tissue responsive to the illuminated light radiation at a certain light detection direction, and to generate measurement data indicative thereof, said light illumination and detection directions are selected to form an angle of at least $2°$.

In some cases, the device further comprises a control unit configured and operable to activate said at least one light source to illuminate the examined tissue, receive and process the measurement data generated by said light detector, and determined based thereon said biological properties.

In some cases, the device further comprising an output unit configured and operable to output data comprising at least one of said biological properties and said measurement data.

In some cases, the output unit comprises a display unit placed on the upper side of the housing and configured and operable to receive and display said output data.

In some cases, the device further comprises an input unit configure and operable to receive input data from a user and transfer said input data to at least one of the control and display units.

BRIEF DESCRIPTION OF THE DRAWINGS

In order to understand the invention and to see how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings like reference numerals are used to indicate corresponding parts, and in which.

DETAILED DESCRIPTION OF EMBODIMENTS

One or more specific embodiments of the present disclosure will be described below with reference to the drawings, which are to be considered in all aspects as illustrative only and not restrictive in any manner. In an effort to provide a concise description of these embodiments, not all features of an actual implementation are described in the specification. Elements illustrated in the drawings are not necessarily to scale, emphasis instead being placed upon clearly illustrating the principles of the invention. This invention may be provided in other specific forms and embodiments without departing from the essential characteristics described herein.

The present invention discloses a reflective optical measurement device designed to improve the magnitudes of optical signals measured from an examined tissue, and their SNR and AC/DC ratios. It is known that a substantial portion of the optical signals measured using reflective measurement devices contain light components reflected from non-perfused tissue layers, that mainly contribute to baseline DC and noise components (i.e., light components that don't contain blood related information) of the measured signals. It is also known that the ratio between the perfused area to non-perfused area which influences the AC/DC ratio may vary from one body organ to another. This is demonstrated in FIGS. 1A and 1B, showing a typical reflective measurement setup 19 configured for measuring optical signals reflected from an examined tissue 15.

The measurement setup 19 comprises a light source 10 and a sensor unit 12, disposed on an outer surface of the examined tissue 15. The sensor unit 12 is also defined as a light detector 12. Typically, the light source 10 and the light detector 12 are placed on a skin region of a subject and arranged such that the light detector 12 receives components of the light emitted from the light source 10 and reflected from different layers S1, S2, . . . , S5, . . . of the examined tissue 15 towards the detector 12. The light source 10 and the light detector 12 are substantially parallel to the surface of the examined tissue 15, such that the direction of light illumination 10r of the light source 10 and the direction of light detection 12r of the light detector 12 are substantially parallel.

Figure 1A:
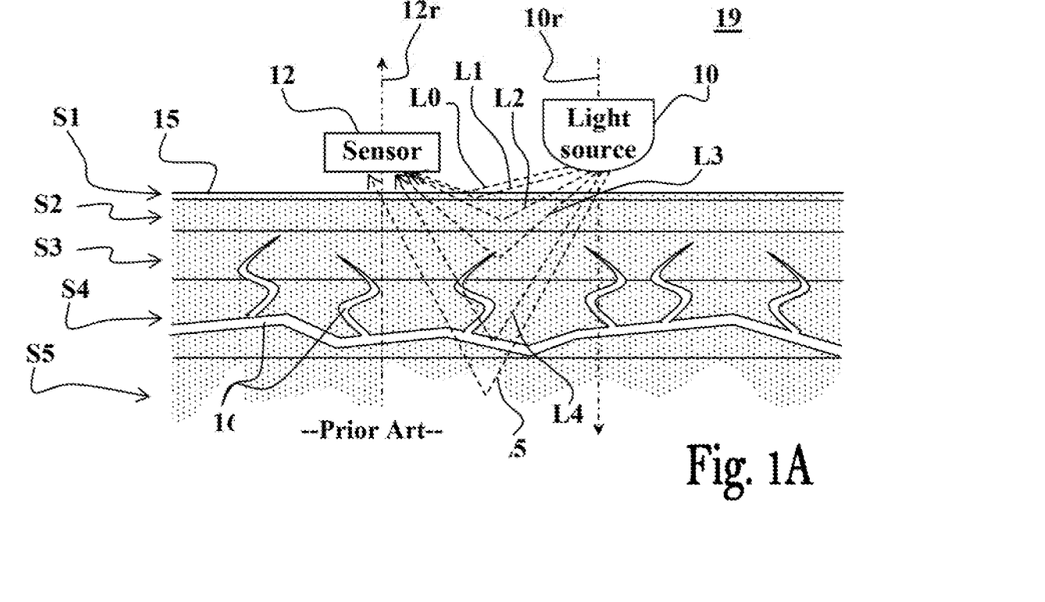
FIGS. 1A and 1B schematically illustrate a conventional reflective measurement device.
Figure 1B:
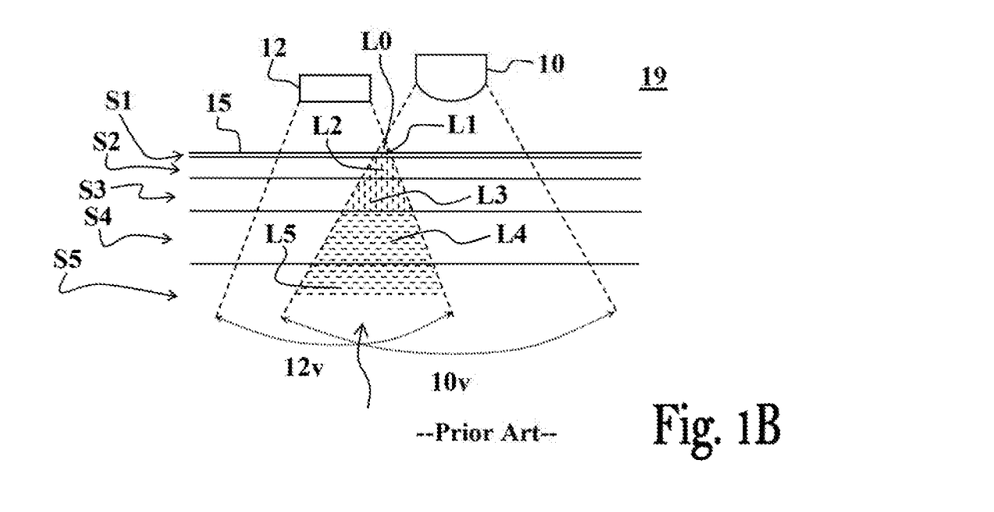

FIG. 1A further exemplifies the scattering of light components reflected from the various layers of the examined tissue 15 in such conventional reflective measurement setups 19. As seen, the light detector 12 in the measurement setup 19 receives light components L0 directly reflected from the outer surface S1 of the skin, light components L1 penetrating the outer surface S1 and reflected from the interior of the stratum corneum, and light components L3 reflected from the granular and spinous cell layers S2 of the skin.

The light components L0 reflected directly from the outer surface of the outermost skin layer S1 do not contain any valuable information. Likewise, as the skin layers S1 and S2, which form the epidermis of the skin (also referred to herein as near-surface tissue layers), don't comprise any blood vessels 16 in them, the light components L1 and L2 penetrating into these non-perfused tissue layers, and reflected from them towards the light detector 12, also do not contain blood related information. Thus the light components L0, L1 and L2, which are combined with the other light components during the optical signal measurements of the light detector 12, do not contribute to the measured optical signals any blood related information (pulsating AC components).

The light components which contribute blood related information to the optical signals measured by the light detector 12 are L3, L4 and L5, which penetrate into the deeper perfused tissue layers S3, S4 and S5 (also referred to herein as remote tissue layers, as they are located relatively remote from the light source). These tissue layers contain blood vessels 16, such that the light components reflected from them towards the light detector 12 introduce pulsating components to the optical signals measured by the light detector 12. Particularly, the light components L3 are reflected from the dermis layer S3, the light components L4 are reflected from the hypodermis (subcutaneous tissue) layer S4, and the light components L5 are reflected from the tissue layers S5 underneath the skin (e.g., muscular tissue).

The light detection scheme of the measurement setup 19 is further exemplified in FIG. 1B, which illustrates light illumination sector 10v of the light source 10, and a light detection sector 12v of the light detector 12. The intersection 17 of the illumination sector 10v and the detection sector 12v represents the portion of the illuminated light that is reflected towards the light detector 12 during the measurements. The portion of sectors intersection 17 located external to the examined tissue 15 is associated with the light components L0 reflected towards the light detector 12 directly from the outer surface S1 of the tissue 15. The portions of sectors intersection 17 located in the near-surface epidermis layers S1 and S2 are associated with the light components from L1 and L2 reflected towards the detector 12 form the non-perfused tissue layers. The portions of sectors intersection 17 located in the remote tissue layers S3, S4 and S5 are associated with the light components from L3, L4 and L5, reflected towards the detector 12 form the perfused tissue layers.

The optical signals measured by the light detector 12 comprise DC components and pulsating AC components. While all the light components L0 to L5 measured by the light detector 12 comprise DC components, only the light components L3 to L5 reflected from the perfused tissue layers contribute pulsating AC components. Therefore, in the optical signal measured by the light detector 12 in conventional measurement setups 19 exemplified in FIGS. 1A and 1B, the portion of the pulsating AC components relative to the portion of the DC components, is substantially small (e.g., about 1/1000 to 1/5000 at the wrist), which thus provide poor signal quality with low SNR and AC/DC ratios.

In order to improve the quality of the optical signals measured by reflective measurement setups it is desired to maximize in the measured optical signals light components that interact with the perfused tissue layers S3, S4 and S5 (i.e., to increase the pulsating AC components that contains blood related information), and minimize in the measured optical signals light components that interact with the non-perfused tissue layers S1 and S2. These objectives are achieved in some of the embodiments disclosed herein by at least one of: (i) increasing as much as possible the optical paths through which the measured light components pass through the examined tissue 15 tissue before they reach the light detector 12, thereby causing them to interact with more of the blood vessels 16 of the examined tissue 15; and (ii) reducing as much as possible measurement of light components that are reflected from the non-perfused tissue layers (e.g., external layers such as the epidermis).

Figure 2A:
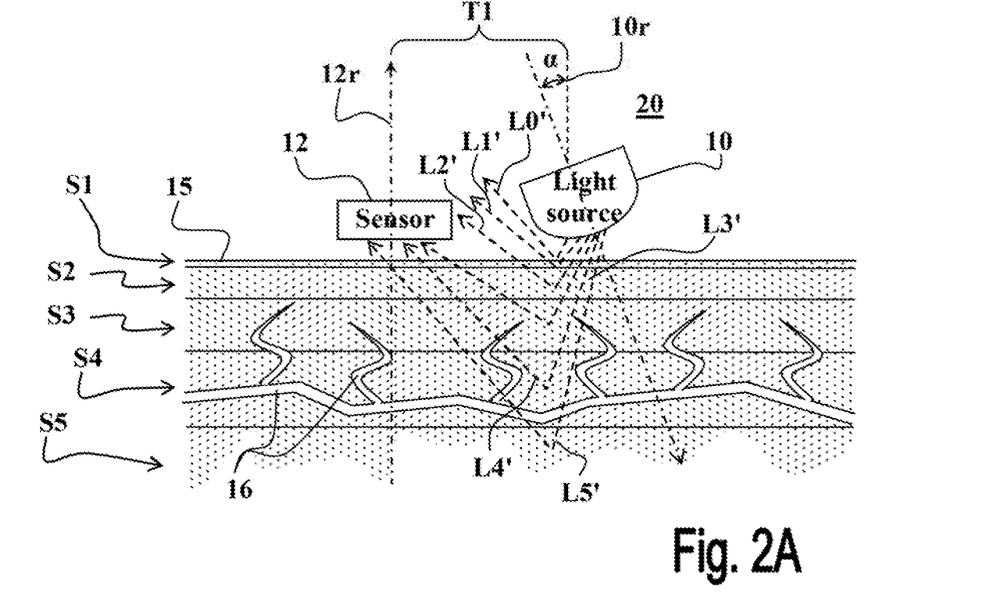
FIGS. 2A and 2B schematically illustrate a reflective measurement setup according to some possible embodiments wherein the light source is located adjacent the light detector.
Figure 2B:
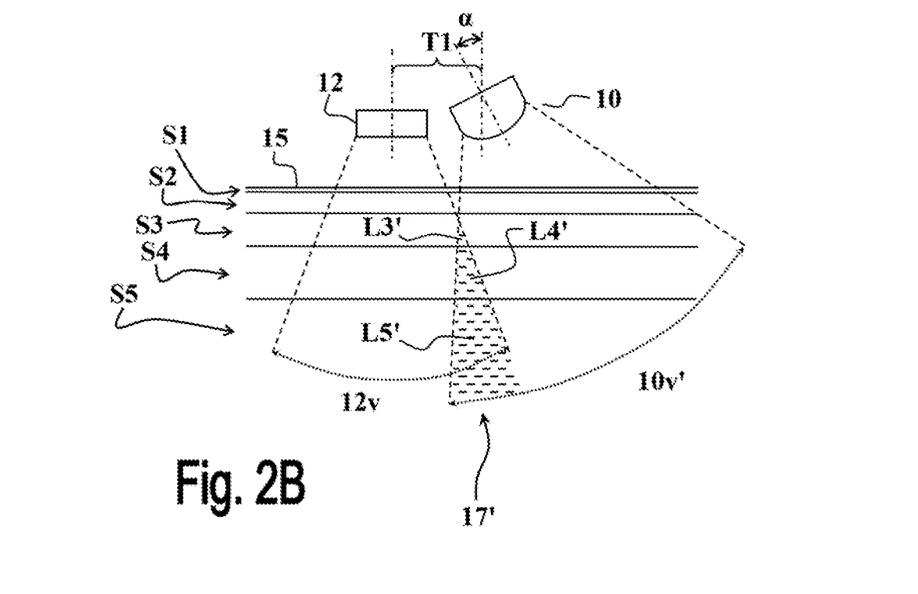

In some embodiments the setup of the reflective measurement setup 20 shown in FIGS. 2A and 2B is used, in which at least one light source 10 (only one is shown in FIGS. 2A and 2B) is placed spaced apart from the light detector 12, and oriented such that the angle α between the direction of light illumination 10r and the direction of light detection 12r is greater than 0° and smaller than 90°, optionally about 20 to 88° (i.e., an angle α of 0° means that light illumination direction 10r and the light detection direction 12r are parallel, for example perpendicular to the examined tissue 15, as shown in FIG. 1, and an angle α of 90° is obtained when the light illumination direction 10r is perpendicular to the light detection direction 12r.

In this non-limiting example the angle between the light detector 12 and the examined tissue 15 results the two being substantially parallel to. Also, as seen, the light detector 12 and at least one light source 10 are located at the same side of the examined tissue 15, wherein the same side is defined as a setup in which the light detector's position is such that the detected light is the light reflected by the body tissue In this reflective measurement setup 20 as the angle α between the light illumination direction 10r and the light detection direction 12r is increased the distance between the light source 10 and the light detector 12 are respectively reduced, and vice versa. For example, and without being limiting, in some embodiment the distance T1 in the reflective measurement setup 20 is about 0.1 to 30 mm (for angles α ranging between 2° to 88°, respectively). Optionally, and in some embodiments preferably, the light detector 12 is substantially parallel to the examined tissue (i.e., the light detection direction 12r is substantially perpendicular to the surface of the examined tissue 15), and the angle α is obtained by properly setting the orientation of the light sources 10 of the measurement setup 20.

As shown in FIGS. 2A and 2B, the angle of orientation of the light source 10 permits locating the light source 10 at relative short distance T1 in the vicinity of the light detector 12, while guaranteeing that the light components L0', L1' and L2', are reflected from the non-perfused tissue layers S1 and S2 with substantially acute angles relative to the light detection direction 12r. Thus the amount of light components L0', L1' and L2' reflected from the non-perfused near-surface tissue layers S1 and S2 towards the light detector 12 is substantially reduced. The angle of orientation enables maintaining a small blood measurement apparatus with improved SNR and AC/DC ratio.

On the other hand, the light components L3', L4' and L5', penetrating into the remote perfused tissue layers, S3, S4 and S5, respectively, are caused to travel greater distances until they are reflected towards the light detector 12 and therefore interact with greater amounts of perfused tissues. Due to the increased optical paths of the light components L3', L4' and L5' reflected from the perfused tissue layers, S3, S4 and S5, the amount of pulsating AC information they contain is substantially increased.

This light detection scheme of the reflective measurement setup 20 is further demonstrated in FIG. 2B showing the intersection 17' of the light illumination sector 10v' with the light detection sector 12v. As seen, the portions of the intersection 17' of the sectors are located only (or mainly, depending on the angle α) in the perfused tissue layers S3, S4 and S5. Accordingly, all of the portions of the intersection 17' are associated with the light components L3', L4' and L5' reflected towards the light detector from the perfused tissue layers.

Accordingly, the baseline DC components in the optical signals measured by the light detector 12 in the reflective measurement setup 20 are substantially reduced, by reducing the amount (or altogether excluding) of light components L0', L1' and L2', reflected from the non-perfused tissue layers S1 and S2. On the other hand, since the optical paths L3', L4' and L5', of the light components reflected towards the light detector 12 from the perfused tissue layers are increased, they interact more intensely with perused tissue and thus contain significantly more blood related information and contribute greater amounts of pulsating AC components to the optical signals measured by light detector 12 (as compared to conventional measurement setup 19 of FIG. 1).

Experiments conducted by the inventors showed that the optical signals measured using the reflective measurement setup 20 provide substantial improvement in the quality of the measured optical signals, and in their SNR and AC/DC ratios. For example, utilizing a reflective measurement device may increase the AC/DC ratio in a factor of 10 or more.

Figure 3A:
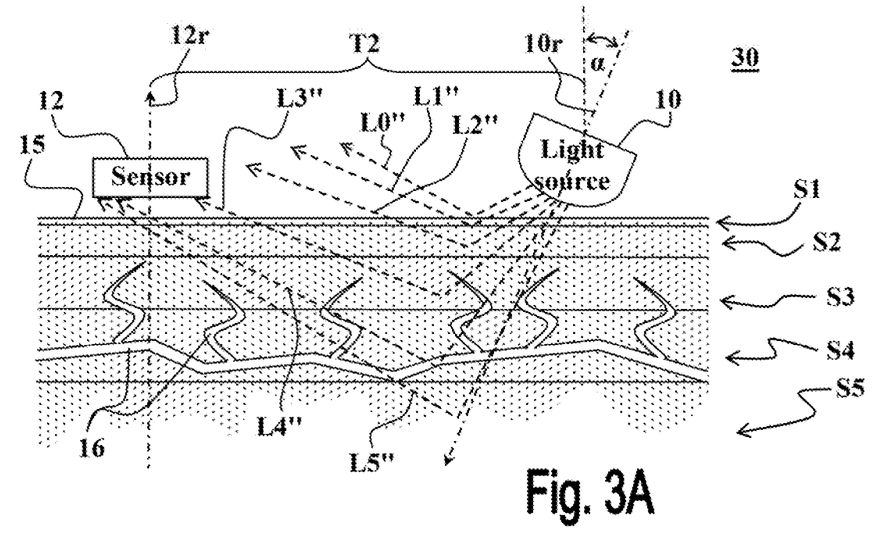
FIGS. 3A and 3B schematically illustrate a reflective measurement setup according to some possible embodiments wherein the light source is relatively remote to the light detector.
Figure 3B:
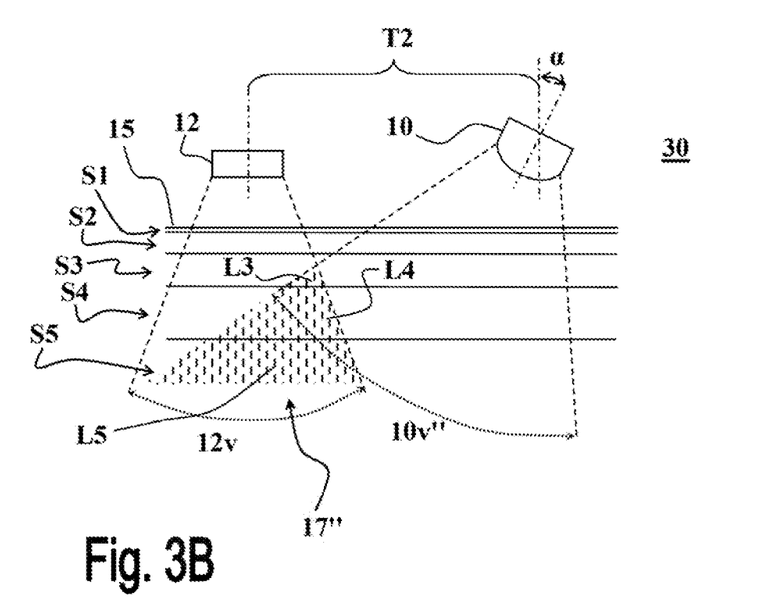

FIGS. 3A and 3B demonstrate another possible measurement setup 30 according to some possible embodiments. In this non-limiting example the at least one light source 10 (one light is shown in FIGS. 3A and 3B) is displaced from the light detector 12 to a relatively remote location over the examined tissue 15, and respectively oriented towards the light detector 12. As exemplified here, the light detector 12 is substantially parallel to the examined tissue 15, and the light detector 12 and the at least one light source 10 are located at the same side of the examined tissue 15. In possible embodiments, the distance T2 between the light source 10 and the light detector 12 is about 0.1 to 30 mm. The angle $\alpha$ between the light illumination direction 10r and the light detection direction 12r is increased as the distance T2 is increased.

Optionally, and in some embodiments preferably, the light detector 12 is substantially parallel to the surface of the examined tissue 15 (i.e., the light detection direction is substantially perpendicular to the tissue surface), and the orientation of the light source 10 is selected to provide suitable angle $\alpha$ between the light illumination and light detection directions e.g., about 2° to 88°. In this arrangement, the light components L1" to L5" are reflected from the respective tissue layers S1 to S5 towards the light detector 12 in obtuse angles. Proper selection of the orientation of the light source 10 with respect to the distance T2 provides that the amount of light components L0", L1" and L2", reflected from the non-perfused tissue layers S1 and S2 and detected by the light detector 12, is substantially/negligibly small, while assuring substantial detection of the light components L3", L4" and L5", reflected from the perfused tissue layers, S3, S4 and S5.

As demonstrated in FIG. 3B, the portions of the intersection 17" of the light detection sector 12v and the illumination sector 10v" are all located in the remote perfused tissue layers S3, S4 and S5. Accordingly, all of the portions of the intersection 17" are associated with the light components L3", L4" and L5" reflected towards the light detector 12 from the perfused tissue layers.

Accordingly, the baseline DC components in the optical signals measured by the light detector 12 in the reflective measurement setup 30 are substantially reduced, by reducing (or altogether excluding) the amount of light components L0", L1" and L2", collected by the light detector 12 from non-perfused tissue layers S1 and S2. On the other hand, since the optical paths, of the light components L3", L4" and L5" reflected towards the light detector 12 from the perfused tissue layers are increased, they interact more intensely with perused tissue and thus contain significantly more blood related information and contribute greater amounts of pulsating AC components to the optical signals measured by light detector 12 (as compared to conventional measurement setup 19 of FIGS. 1A and 1B).

Figure 4:
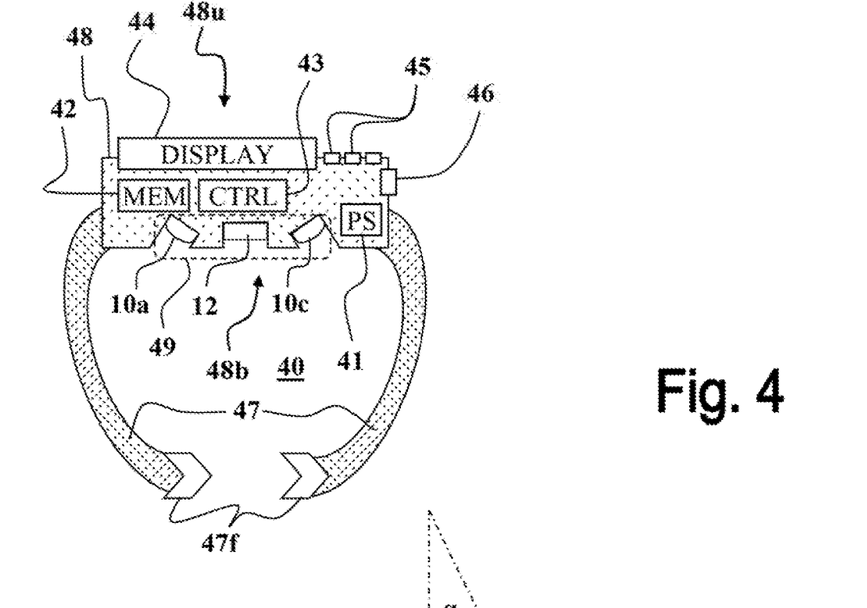
FIG. 4 schematically illustrates a wearable device for measuring biological properties according to some possible embodiments.

Experiments conducted by the inventors showed that the optical signals measured using the reflective measurement configuration 30 provides substantial improvement in the quality of the measured optical signals, and in their SNR and AC/DC ratios. For example, utilizing a reflective measurement device may increase the AC/DC ration in a factor of 10 or more FIG. 4 schematically illustrates a wearable device 40 comprising a reflective measurement setup 49 according to some possible embodiments, configured for measuring biological properties of a subject. In this non-limiting example, the wearable device 40 comprises a housing 48 and one or more straps 47 (two straps are shown in FIG. 4), having respective fastening means 47f at their ends, configured for attachment of the wearable device 40 over a body part/organ of the examined subject (e.g., over the wrist, like a watch). A bottom side 48b of the housing 48 comprises the measurement setup 49, which in this example comprises two light sources 10a and 10c mounted adjacent to the light detector 12, and tilted such that their light illumination directions are directed away from the light detector 12, i.e., as in the measurement setup 20 shown in FIG. 2.

The measurement setup 49 is designed to place the light sources 10a and 10c, and the light detector 12, at the same side of the examined tissue, and to place the light detector 12 over the examined tissue substantially parallel to its surface. Although the wearable device 40 comprises only two light sources 10a and 10c, it should be clear that it may comprise additional light sources e.g., as exemplified in FIG. 5.

The housing 48 comprises a control unit 43 configured and operable to operate the light sources 10a and 10c to illuminate tissue of body part/organ on which the device 40 is worn, and receive from the light detector 12 data and/or signals indicative of the light components reflected from the examined tissue and received by the light detector 12 responsive to the light illuminated by the light sources 10a and 10c. The control unit 43 may further be configured to process the data/signals received from the light detector.

In some embodiments the light sources 10a and 10c are configured and operable to illuminate the examined tissue with light of two or more wavelengths, as may be needed for determining certain blood properties/parameters. In this case the control unit 43 is further configured to operate the light sources 10a and 10c to illuminate the examined tissue with such light radiation of one or more wavelengths, and receive from the light detector 12 corresponding data/signals indicative of the light components reflected from the examined tissue towards the light detector 12 responsive to the illuminated light.

The housing 48 may further comprise a power source 41 (e.g., one or more chargeable batteries), and a memory unit 42 (e.g., RAM, ROM, FLASH) comprising one or more programs, and/or data, as may be needed for carrying out measurements by the measurement setup 49. The upper side 48u of the housing 48 may comprise a display unit 44 (e.g., LCD) electrically coupled to the control unit 43 and configured and operable to display measurement results and/or other data, thereon. The upper side 48u of the housing 48 may further comprise an input unit 45 (e.g., comprising a keypad and/or one or more press buttons) configured and operable to provide the control unit 43 with inputs from a user of the wearable device 40.

The wearable device 40 may further comprise a data communication interface 46 for communicating data between the control unit 43 and an external computer system (not shown e.g., a personal computer—PC). The data communication interface 46 may be configured and operable to communicate with external devices wirelessly (e.g., by WiFi, Bluetooth, or Zigbee), and/or over wire lines/bus (e.g., using serial communication such as universal asynchronous receiver/transmitter—UART/universal serial bus—USB, or parallel bus lines such as IEEE 1284). The data communication interface 46 may be further configured to electrically couple the wearable device 40 to an external power source (not shown e.g., mains power grid) for recharging the power source 41 of the wearable device 40. The data communication interface 46 may be further used to load data and/or programs into the memory unit 42 of the wearable device 40 from an external computer system, if so needed.

In some embodiment, the measured optical signals can be further improved by increasing the flux of light illuminated towards the examined tissue, for example, by using two or more light sources, as exemplified in FIG. 4 hereinabove. The light sources may be angularly spaced apart on a perimeter encircling the light detector 12, radially spaced apart therefrom and oriented with respect to said radial distance such that the angles between the light illumination and light detection directions increases the travel paths of the detected light components through the examined tissue.

Figure 5:
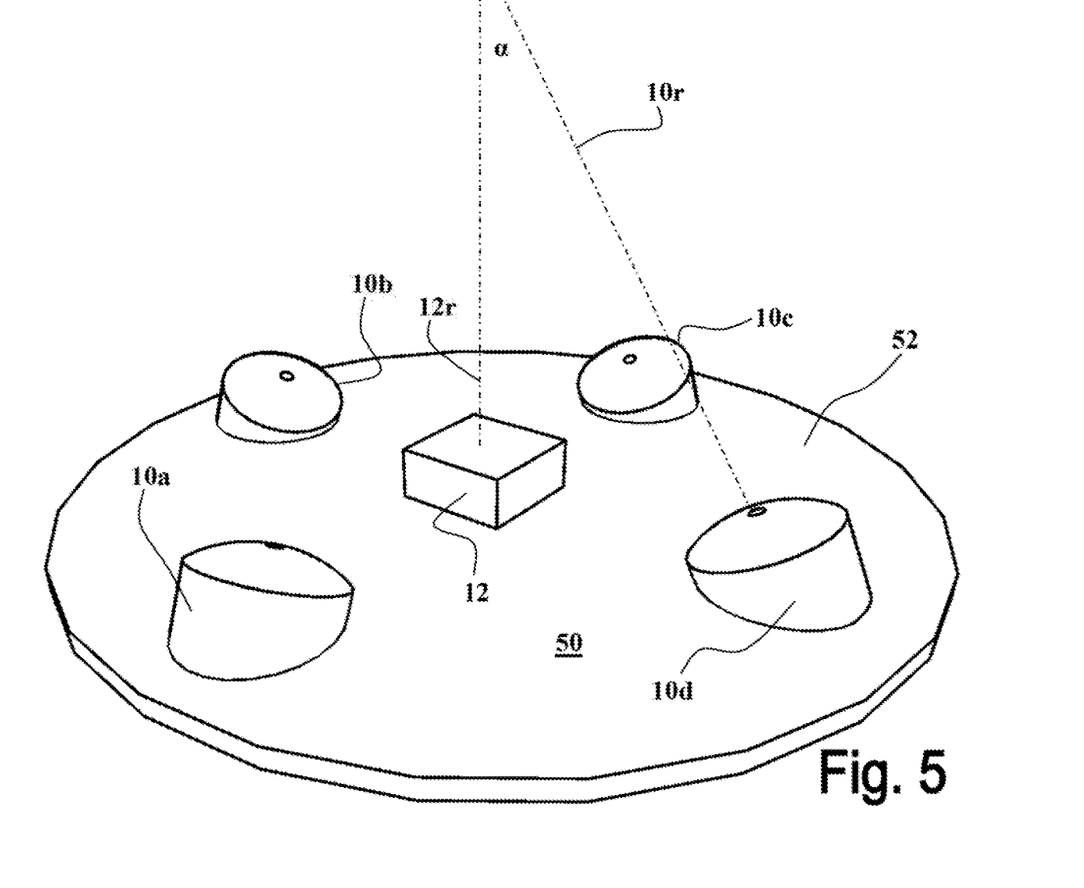
FIG. 5 exemplifies a reflective measurement device according to some possible embodiments utilizing several light sources.

FIG. 5 exemplifies a reflective measurement device 50 according to some possible embodiments comprising a single detector 12 and four light sources 10a, 10b, 10c and 10d (collectively referred to herein as light sources 10). The light sources 10 are mounted on the support member 52 displaced and remote from the light detector 12, and their orientations are properly set such that their light illumination directions are directed toward the light detector 12 (as in the measurement setup 30 shown in FIG. 3), to provide a suitable angle α between the light illumination directions 10r and the light detection direction 12r. This arrangement allows placing the light sources 10 and the light detector 12 at the same side of the examined tissue, and the light detector 12 substantially parallel to the tissue surface.

In a similar fashion, the light sources 10 may be located on support member 52 adjacent to the light detector 12, and tilted such that their light illumination directions are directed away from the light detector 12, to provide a suitable angle α between the light illumination directions 10r and light detection direction 12r (as in the measurement setup 20 shown in FIG. 2).

Figure 6:
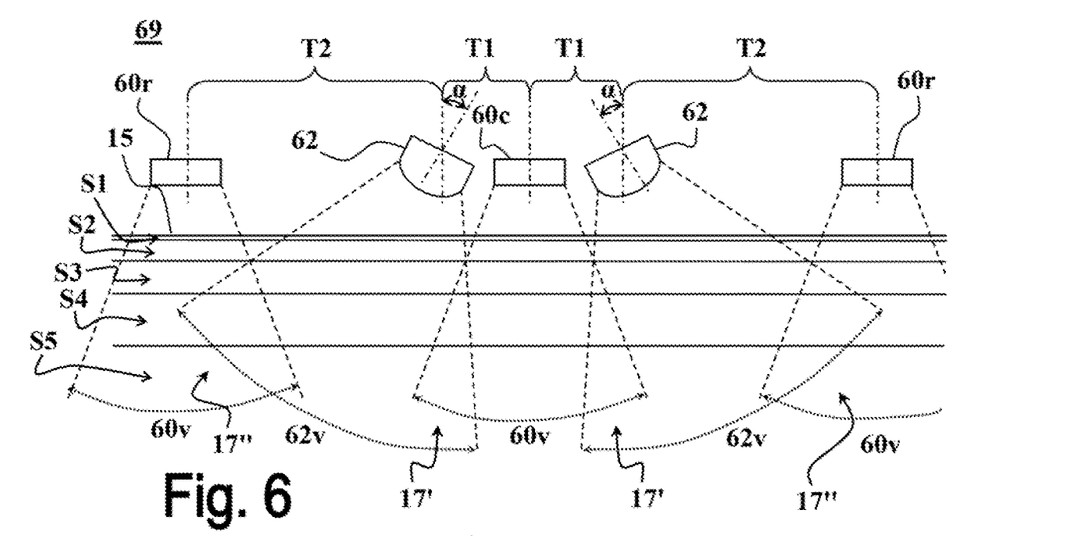
FIG. 6 schematically illustrate a reflective measurement setup according to possible embodiments utilizing several light detectors.

FIG. 6 exemplifies a reflective measurement setup 69 that combines principles of the measurement setups 20 and 30 shown in FIGS. 2A-B and 3A-B, respectively. In this non-limiting example two light sources 62 are placed in a vicinity of a central light detector 60c with distances T1 there between. The two light sources 62 are oriented such that their light illumination directions are directed away from the central light detector 60c, so as to form angles α between their light illumination direction and the light detection direction of the central detector 60c. With this arrangement of the light sources 62 and the central light detector 60c two intersections 17' are formed between the detection sector 60v of the central light detector 60c and the illumination sectors 62v of the light sources 62.

The measurement setup 69 further comprises two peripheral light detectors 60r, each associated with a respective one of the light detectors 62 and located with a distance T2 therefrom. The tilt angle α of the light detectors 62 and the distance T2 of their respective peripheral light detectors 60r, are selected such that two intersections 17" are respectively formed between the detection sectors 60v of the peripheral light detector 60r and the illumination sectors 62v of their respective light sources 62. The ranges of the distances T1 and of the angles α are substantially as defined hereinabove with reference to FIGS. 2A-B, and the ranges of the distances T2 are substantially as defined hereinabove with reference to FIGS. 3A-B, for example 0.1 mm to 30 mm.

Figure 7:
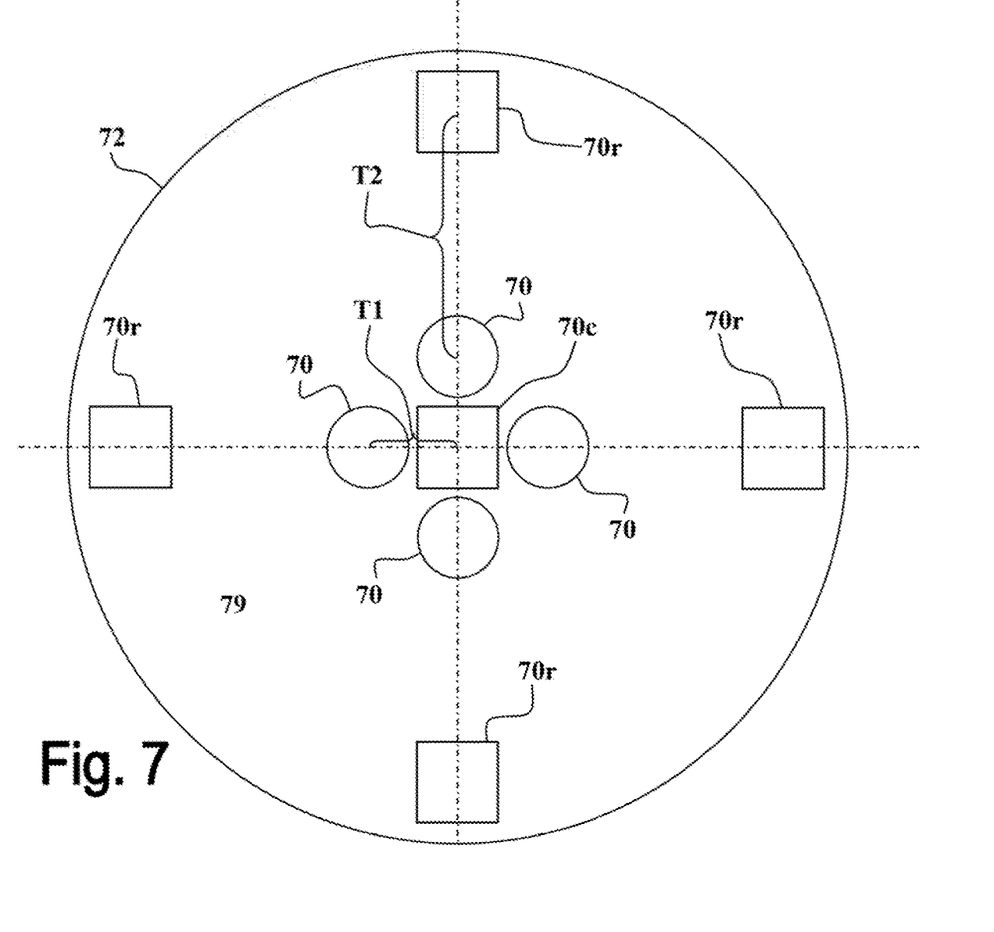
FIG. 7 exemplifies a reflective measurement setup according to possible embodiments utilizing several light detectors.

FIG. 7 exemplifies a configuration of a reflective measurement device 79 comprising four light sources 70 arranged around a central light detector 70c, and four peripheral light detectors 70r, each associated with a respective one light source 70. The reflective measurement device 79 is a two-dimensional implementation of the measurement setup 69 shown in FIG. 6. Namely, the light sources 70 are placed in the vicinity of the central light detector 70c with distances T1 therefrom, and tilted away therefrom such that angles are formed between the light detection direction of the light detectors 70c and the light illumination directions of the light sources 70. In this way, four intersections (similar to 17' disclosed above) are defined between the light detection sector of the central light detector 70c and the illumination sectors of the light sources 70, and four intersections (similar to 17" disclosed above) are defined between the light detection sectors of the peripheral light detectors 70r and the illumination sectors of their respective light sources 70.

The reflective measurement device 79 is designed to place all light sources and detectors at the same side of the examined tissue, and place the light detectors substantially parallel to the surface of the examined tissue. The ranges of the distances T1 and of the angles α are substantially as defined hereinabove with reference to FIGS. 2A-B, and the ranges of the distances T2 are substantially as defined hereinabove with reference to FIGS. 3A-B.

In some embodiments one or more optical elements are coupled to the light source 10 to provide a predefined angle of light illumination (i.e., the angle of sector 10v' and 10v" in FIGS. 2B and 3B). For example, one or more lenses (not shown) may be optically coupled to the light source to provide an illumination angle of about 15° to 30° and reduce light dispersion of the light source 10. Additionally, or alternatively, in possible embodiments the light source 10 may be designed to provide such the desired illumination angles without using lenses e.g., by collimators. The light source 10 may be implemented using one or more light emitting diodes (LEDs). For example, and without being limiting, in some possible embodiments the light source 10 comprises LEDs for emitting light radiation in at least one of the wavelengths within a range between 400 nm and 1500 nm (Nanometer), which may be used for determining at least one of the biological properties, respectively: at least one of heart rate, oxygen saturation, hemoglobin level, blood pressure, cardiac output, stroke volume, perspiration, glucose/sugar level, and bilirubin level, fat level.

In standard devices the light source direction and light detector direction are parallel and perpendicular to the surface of the examined tissue as shown in FIG. 1. The present invention includes all the combinations of changing this configuration. The configurations of the present invention include:

1. The light detector in the same position and light source with inner or outer angle relative to an imaginary line perpendicular of the examined tissue,
2. The light source is fixed and the light detector has the above angle,
3. Both elements have different angles, for example the light source is directed towards the light detector and the light detector is directed away from the light source, both the detector and the source are directed towards the other or away from the other;

4. The illumination and detection directions are parallel and not perpendicular to the examine tissue surface.

Alternatively, the light source 10 may be implemented by a radiation source capable of simultaneously emitting light radiation in a predefined radiation spectrum range covering the one or more wavelength ranges needed for determining the biological properties. For example, and without being limiting, one or more filtering device optically coupled to the light source 10 may be used to selectively illuminate the examined tissue with light radiation in a specific wavelength range at a time, as may be required for determining a specific biological property by the device.

It is note that the reflective measurement techniques disclosed herein are also very useful for portable as the improved SNR and AC/DC ratios they provide mitigates signals distortions that are induced in the measured signals due to movements of the body part/organ to which the device is attached.

Figure 8:
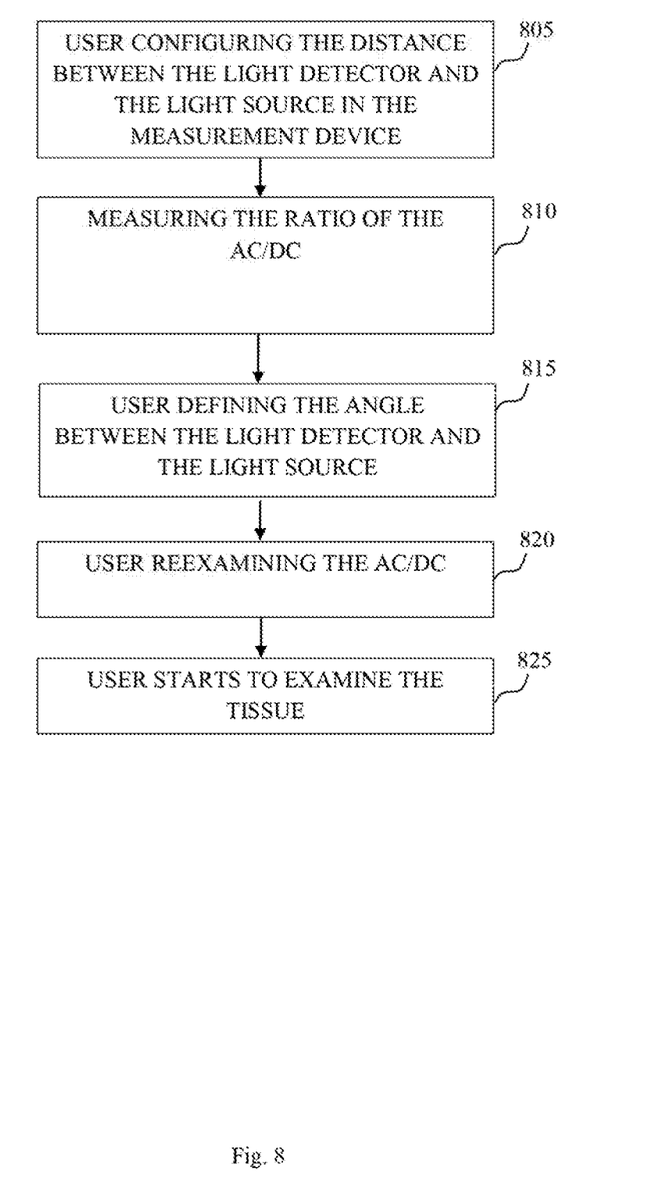
FIG. 8 shows a method to configure the reflective measurement device, according to exemplary embodiments of the invention.

FIG. 8 shows a method to configure the reflective measurement device, according to exemplary embodiments of the invention. In step 805 a user utilizing the reflective measurement device may configure the distances between the light detector and the light source. The light source may be configured in a certain distances relative to a light detector unit of the measurement device. In step 810, the user may measure the AC/DC ratio with a specific examined tissue, in the configured distance between the light source and light detector. In some cases, the measurement process defined in step 810 may take place with number of tissue types, various wavelengths, various measured properties and additional parameters of the device. In step 815, the user may configure the angle between the light source and the light detector. The angle configuration may be in accordance to the AC/DC ratio received in step 810. For example, different wavelengths may be reflected differently from the same examined tissue, the user may change the angle between the light detector and the light source, check the AC/DC ratio and in some cases, change the angle again until the received AD/DC rate reaches a predefined or desired threshold or value. The angle configuration preformed in step 815 may be achieved by tilting the light detector and the light source laterally, upwards and/or downwards, or in other words closer or farther away from the examined tissue. In step 820, the user may reexamine the AC/DC ratio and preform changes in the angle between the light source and the light detector. For example, the user may tilt the light detector upwards or downwards and thereby change the AC/DC rate received by the reflective measurement device. In some case, the user may go back to step 805 and change the distances between the light source and the light detector in order to achieve an optimal AC/DC rate. In step 825, the user may start to examine the tissue after the angle and distance are determined. Thus, the user may measure the AC/DC rate in several cases along the method described above. In some cases, different wavelengths may be emitted to the examined tissue, and then be detected by different light detectors. In some other cases, more than one tissue may be examined and the user may need to set the reflective measurement device on different organs, or limbs. The user may also be required to conduct steps 805, 810, 815, and 820 several times on various examined tissues. The techniques disclosed herein are applicable to almost any type of optical measurement of blood properties, parameters and/or analytes, employing effects of optical absorption and scattering of electromagnetic radiation in a living tissue. Particularly, the techniques disclosed herein are useful for measuring pulsating signals, as typically obtained in types of non-invasive blood measurements, such as, but not limited to, pulse oximetry, photoplethysmogram (PPG) measurements, and suchlike. For example, and without being limiting, the optical measurement techniques disclosed herein may be useful for measuring blood pulses, oxygen ($O_2$) saturation, hemoglobin levels, glucose/sugar levels, bilirubin levels, and suchlike.

The method of the present invention enables emission of various wavelengths and measurements of various properties. Some wavelengths are reflected differently from the same examined tissue. Hence, the present invention also disclosed selecting an optimal combination of angle between the light emitter and light detector as well as the distance between them.

As described hereinabove and shown in the associated Figs., the present invention provides reflective measurement configurations for measuring biological properties of an examined tissue/subject with substantially improved SNR and AC/DC ratios. While particular embodiments of the invention have been described, it will be understood, however, that the invention is not limited thereto, since modifications may be made by those skilled in the art, particularly in light of the foregoing teachings. As will be appreciated by the skilled person, the invention can be carried out in a great variety of ways, employing more than one technique from those described above, all without exceeding the scope of the invention.

We claim:

1. A device for measuring biological properties of an examined tissue, the device comprising:
    at least one light source configured and operable to illuminate the examined tissue with light radiation of one or more wavelengths with a direction of the at least one light source defined by a longitudinal and central axis thereof; and
    a light detector configured to be located at a same side of said examined tissue and configured to receive light components of said one or more wavelengths reflected from the examined tissue in response to the illuminated light radiation with a direction of the at least one light source defined by a longitudinal and central axis thereof, and to generate measurement data indicative thereof;
    wherein, at least one light source direction is positioned at an angle of at least 2 degrees from the direction of light detector imaginary line perpendicular to the examined tissue or form an angle of at least 2 degrees between the light source direction and light detector direction, and wherein the position of the light source is configured to maximize the ratio value between light waves reflected from blood vessels of the examined tissue and the combination of light waves reflected from other parts of the examined tissue;
    wherein the direction of the at least one light source is oriented away from the direction of the light detector;
    wherein a distance between the at least one light source and the light detector is optimized relatively to the angle formed between the at least one light source direction and the direction of light detector imaginary line perpendicular to the examined tissue to collect an optimized signal from the blood vessel.

2. The device of claim 1 wherein the direction of the light detector is perpendicular to the surface of the examined tissue and the direction of the at least one light source is positioned at an angle of at least 2 degrees from the direction of the light detector.

3. The device of claim 1 wherein the direction of the at least one light source is perpendicular to the surface of the examined tissue and the direction of the light detector is positioned at an angle of at least two degrees from the direction of the at least one light source.

4. The device of claim 1, wherein the at least one light source is parallel to the light detector and is positioned at an angle of at least 2 degrees relative to an imaginary line perpendicular to the examined tissue.

5. The device of claim 1, wherein the at least one light source is not parallel to the light detector, wherein each of the light source and the light detector forms an angle of at least 2 degrees relative to an imaginary line perpendicular to the examined tissue.

6. The device of claim 1, wherein the distance between the at least one light source and the light detector is 0.1 to 30 mm.

7. The device of claim 1, wherein the angle formed between the light illumination and detection directions is decreased with an increase in a distance between the at least one light source and the light detector.

8. The device of claim 1, further comprising two or more light sources encircling the light detector.

9. The device of claim 1, wherein the biological properties include at least one of heart rate, oxygen saturation, hemoglobin level, blood pressure, cardiac output, stroke volume, perspiration, glucose/sugar level, and bilirubin level, fat level.

10. The device of claim 1, wherein the device is a wearable device comprising a housing having bottom and upper sides and strapping means for attaching said bottom side of the housing to an examined tissue of said subject.

11. The device of claim 10, wherein the housing comprises:
at said bottom side of said housing, the at least one light source configured and operable to illuminate said examined tissue with light radiation of one or more wavelengths with a direction of the at least one light source defined by a longitudinal and central axis thereof, and the light detector configured and operable to receive light components of said one or more wavelengths reflected from the examined tissue responsive to the illuminated light radiation, and to generate measurement data indicative thereof, said direction the light source and the direction of the light detector defined by a longitudinal and central axis thereof are selected to form an angle of at least two degrees.

12. The device of claim 10, further comprises a control unit configured and operable to activate said at least one light source to illuminate the examined tissue, receive and process the measurement data generated by said light detector, and determined based thereon said biological properties.

13. The device of claim 10 further comprising an output unit configured and operable to output data comprising at least one of said biological properties and said measurement data.

14. The device of claim 13 wherein the output unit comprises a display unit placed on the upper side of the housing and configured and operable to receive and display said output data.

15. The device of claim 10, further comprising an input unit configured and operable to receive input data from a user and transfer said input data to at least one of the control and display units.

16. A method operable on a device comprising at least one light source configured and operable to illuminate an examined tissue with light radiation of one or more wavelengths with a direction of the at least one light source defined by the longitudinal and central axis thereof and a light detector configured to be located at a same side of said examined tissue, wherein the light detector is configured to receive light components of said one or more wavelengths reflected from the examined tissue in response to the illuminated light radiation for measuring biological properties of an examined tissue, the method comprising:
measuring, by the device, the value of the ratio between light waves reflected from blood vessels of the examined tissue and the combination of light waves reflected from other parts of the examined tissue;
configuring the angle between the at least one light source and the light detector to maximize the ratio value between light waves reflected from blood vessels of the examined tissue and the combination of light waves reflected from other parts of the examined tissue, wherein at least one light source direction is positioned at an angle of at least 2 degrees from the direction of light detector imaginary line perpendicular to the examined tissue or form an angle of at least 2 degrees between the light source direction and light detector direction;
starting to operate the device in order to examine the examined tissue;
wherein the direction of the at least one light source is oriented away from the direction of the light detector;
wherein a distance between the at least one light source and the light detector is optimized relatively to the angle formed between the at least one light source direction and the direction of light detector imaginary line perpendicular to the examined tissue to collect an optimized signal from the blood vessel.

17. The method of claim 16, wherein configuring the angle between the at least one light source and the light detector comprises reaching a predefined threshold value of the ratio between light waves reflected from blood vessels and the combination of light waves reflected from other parts of the examined organ tissue.

18. The device of claim 1, wherein the angle between the at least one light source and the light detector is configured to reach a predefined threshold value of the ratio between light waves reflected from blood vessels and the combination of light waves reflected from other parts of the examined organ tissue.

* * * * *